United States Patent
Paek

(10) Patent No.: US 10,799,861 B2
(45) Date of Patent: Oct. 13, 2020

(54) BIOCHEMICAL-IMMUNOLOGICAL HYBRID BIOSENSOR AND SENSOR SYSTEM INCLUDING THE SAME

(71) Applicant: KOREA UNIVERSITY RESEARCH AND BUSINESS FOUNDATION, SEJONG CAMPUS, Sejong-si (KR)

(72) Inventor: Se-Hwan Paek, Seoul (KR)

(73) Assignee: KOREA UNIVERSITY RESEARCH AND BUSINESS FOUNDATION, SEJONG CAMPUS, Sejong-si (KR)

(*) Notice: Subject to any disclaimer, the term of this patent is extended or adjusted under 35 U.S.C. 154(b) by 405 days.

(21) Appl. No.: 15/820,719

(22) Filed: Nov. 22, 2017

(65) Prior Publication Data
US 2018/0141041 A1    May 24, 2018

(30) Foreign Application Priority Data
Nov. 24, 2016 (KR) .................. 10-2016-0157033

(51) Int. Cl.
*B01L 3/00* (2006.01)
*G01N 33/558* (2006.01)
(Continued)

(52) U.S. Cl.
CPC ..... *B01L 3/5023* (2013.01); *C12Y 113/12004* (2013.01); *G01N 33/54366* (2013.01);
(Continued)

(58) Field of Classification Search
CPC .......... B01L 3/5023; B01L 2300/0816; B01L 2300/0819; B01L 2300/0887; B01L 2400/0406; B01L 2300/0654; B01L 2300/0825; B01L 2300/069; G01N 33/54366; G01N 33/74; G01N 33/6893; G01N 33/558; G01N 2333/908; G01N 2333/90241; G01N 2333/585;
(Continued)

(56) References Cited

U.S. PATENT DOCUMENTS

| 5,354,692 A | * | 10/1994 | Yang | ................... | G01N 33/558 422/412 |
| 2004/0214253 A1 | * | 10/2004 | Paek | ..................... | C12Q 1/001 435/7.92 |
| 2016/0080548 A1 | * | 3/2016 | Erickson | ........... | H04M 1/72527 455/556.1 |

FOREIGN PATENT DOCUMENTS

| KR | 20040093048 | 11/2004 |
| KR | 20140070956 | 6/2014 |

OTHER PUBLICATIONS

McDonnell, et al. (2009) "Cardiac biomarkers and the case for point-of-care testing." Clinical Biochemistry No. 42: 549-561.
(Continued)

*Primary Examiner* — Sally A Merkling
(74) *Attorney, Agent, or Firm* — Harness, Dickey & Pierce, P.L.C.

(57) ABSTRACT

Disclosed is a biochemical-immunological hybrid biosensor. The biochemical-immunological hybrid biosensor includes a reaction strip in the form of a porous membrane through which a sample moves by capillary action. The reaction strip can simultaneously measure heterogeneous multiple biomarkers through both a biochemical analysis and an immunoassay in an independent manner based on membrane chromatography to diagnose a particular disease.

11 Claims, 10 Drawing Sheets

(51) Int. Cl.
G01N 33/68 (2006.01)
G01N 33/74 (2006.01)
H04N 9/07 (2006.01)
H04N 5/225 (2006.01)
G01N 33/543 (2006.01)
C12Q 1/26 (2006.01)

(52) U.S. Cl.
CPC ....... *G01N 33/558* (2013.01); *G01N 33/6893* (2013.01); *G01N 33/74* (2013.01); *H04N 5/2254* (2013.01); *H04N 5/2256* (2013.01); *H04N 9/07* (2013.01); *B01L 2300/069* (2013.01); *B01L 2300/0654* (2013.01); *B01L 2300/0816* (2013.01); *B01L 2300/0819* (2013.01); *B01L 2300/0825* (2013.01); *B01L 2300/0887* (2013.01); *B01L 2400/0406* (2013.01); *C12Q 1/26* (2013.01); *G01N 2333/4737* (2013.01); *G01N 2333/585* (2013.01); *G01N 2333/908* (2013.01); *G01N 2333/90241* (2013.01); *G01N 2800/26* (2013.01)

(58) Field of Classification Search
CPC ....... G01N 2333/4737; G01N 2800/26; G01N 33/68; G01N 33/52; H04N 5/2254; H04N 5/2256; H04N 9/07; C12Y 113/12004; C12Q 1/26
See application file for complete search history.

(56) References Cited

OTHER PUBLICATIONS

Samraj, et al. (2013) "Role of biomarkers in sepsis care." National Institutes of Health; Shock; 40(5): 358-365.

* cited by examiner

BIOCHEMICAL-IMMUNOLOGICAL HYBRID BIOSENSOR AND SENSOR SYSTEM INCLUDING THE SAME

CROSS-REFERENCE TO RELATED APPLICATION

This application claims priority to Korean Patent Application No. 10-2016-0157033 filed on Nov. 24, 2016. The entire disclosure of the application identified in this paragraph is incorporated herein by reference.

FIELD

The present invention relates to a biosensor and a sensor system including the same. More specifically, the present invention relates to a biosensor, in the field of diagnostic testing, capable of simultaneously measuring heterogeneous multiple biomarkers detected by both a biochemical analysis and an immunoassay in an independent manner based on membrane chromatography, and a sensor system including the biosensor.

BACKGROUND

Membrane chromatography offers the advantages of a short turn-around time, simplicity, and practicality compared to conventional in vitro diagnostics in the field of point-of-care-testing (POCT) (Clin. Biochem., 2009, 42, pp 549-561). Particularly, a lateral flow immuno-chromatographic assay (LF-ICA) for which a membrane strip is used is one of the most practical formats and is widely used for POCT due to its ability to detect the presence or absence and the concentration of analytes in a sample within a short time even without using expensive equipment.

LF-ICA is applied to the development of immunosensors for point-of-care-testing. In LF-ICA, a nano-sized material, such as colloidal gold, with a large extinction coefficient is employed to produce a color, which can be recognized by the naked eye, and it takes 15 min for all assay processes to complete.

However, inadequate sensitivity of LF-ICA based on gold nanoparticles for the detection of very small amounts of substances in sample (for example, blood sample) needs to be improved. This need leads to the introduction of sensitive signaling substances or materials as tracers such as enzymes or fluorescent dyes.

Such conventional immunosensors for POCT are used for the measurement of protein biomarkers and exhibit excellent analytical performance with high sensitivity but fail to acquire information on biochemical markers necessary to make a clinical decision regarding particular diseases. For example, the diagnosis of sepsis requires information on protein markers through antigen-antibody reactions and biochemical markers such as lactate, but biochemical analysis through enzyme reactions cannot be expected in the conventional immunosensors for POCT. Thus, the use of separate assay systems is inevitable for the measurement of heterogeneous biomarkers.

Consequently, the measurement of heterogeneous biochemical-protein biomarkers through different systems requires a long time for analysis, and the different analytical conditions and environments deteriorate diagnostic reliability. When blood samples are frequently collected, patients are increasingly subjected to pain, which is likely to be physically stressful, particularly for infants and the elderly. In such case, limited samples such as blood samples cannot be efficiently used. Furthermore, it is difficult to simultaneously measure disease-related biomarkers in several patients under urgent situations, for example, in emergency rooms of large hospitals.

Thus, there is an urgent need for a solution to the problems of conventional immunosensors.

SUMMARY

The present invention has been made in view of the problems of the prior art, and it is one aspect of the present invention to provide a biosensor that can simultaneously measure heterogeneous multiple biomarkers through both a biochemical analysis and an immunoassay in an independent manner based on membrane chromatography to diagnose a particular disease.

It is a further aspect of the present invention to provide a sensor system that captures color signals, produced from a biosensor, through a smart device and converts the image into digital data.

A biochemical-immunological hybrid biosensor according to an embodiment of the present invention includes a reaction strip in the form of a porous membrane through which a sample moves by capillary action wherein the reaction strip includes: a sample transfer pad having a predetermined length and along which the sample is transferred from one end to the other in the lengthwise direction; a sample addition pad absorbing the sample loaded from the outside; a conjugate pad including detection antibodies specifically binding to protein markers in the sample and a tracer generating color signals for immunoreactions with the protein markers and connecting one end of the sample transfer pad to the sample addition pad; one or more immunoreaction zones, formed on the sample transfer pad, including capture antibodies specifically binding to the protein markers; at least one biochemical reaction zone, spatially separated from the sample transfer pad, including a chromogenic substrate generating a color signal for a biochemical reaction and at least one enzyme producing a product, reacting with the chromogenic substrate, from a biochemical marker in the sample which is received from at least one of the sample transfer pad, the sample addition pad, and the conjugate pad, and where a biochemical reaction occurs independently from the reactions in the immunoreaction zones; and a sample absorption pad arranged at the other end of the sample transfer pad to absorb the sample transferred along the sample transfer pad.

The biochemical reaction zone may be provided in plurality.

The reaction strip further includes at least one biochemical reaction pad extending outward from at least one of the sample transfer pad, the sample addition pad, and the polymer pad, and the biochemical reaction zone is arranged on one side of the biochemical reaction pad.

The conjugate pad is disposed on one end of the sample transfer pad, the sample addition pad is disposed on the other end of the conjugate pad, and the sample absorption pad is disposed on the other end of the sample transfer pad.

The number of the immunoreaction zones is equal to or greater than 2 and the capture antibodies bind to the corresponding protein markers in a one-to-one relationship in the immunoreaction zones.

The protein markers are C-reactive protein (CRP) and procalcitonin (PRT), the biochemical marker is lactate, the enzyme is an enzyme complex of lactate oxidase (LOX) and horseradish peroxidase (HRP), the chromogenic substrate is potassium iodide, and the hybrid biosensor diagnoses sepsis.

The biochemical-immunological hybrid biosensor further includes a substrate addition pad disposed adjacent to one lateral side of the sample transfer pad to supply a substrate loaded from the outside and a substrate absorption pad disposed adjacent to the other lateral side of the sample transfer pad to absorb the substrate transferred across the sample transfer pad.

The biochemical-immunological hybrid biosensor further includes a cartridge having an accommodation space in which the reaction strip is arranged, a detection window through which the immunoreaction zone and the biochemical reaction zone are exposed, and a sample injection port through which the sample is loaded into the sample addition pad.

A sensor system according to an embodiment of the present invention includes: the biochemical-immunological hybrid biosensor; a smart device in which a camera capable of capturing color signals from the immunoreaction zones or a color signal from the biochemical reaction zone as an image is accommodated; and a smart device holder having a slot into which the biochemical-immunological hybrid biosensor is inserted and adapted to hold the smart device.

The sensor system further includes a light source arranged in the smart device holder to emit light.

The captured image of the color signals is converted into digital data by an application on the smart device.

The sensor system further includes a focusing lens arranged between the camera and the immunoreaction zone or the biochemical reaction zone to control the focal distance of the camera.

The features and advantages of the present invention will become apparent from the following description with reference to the accompanying drawings.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

According to the present invention, the immunoreaction zones where information on protein markers through antigen-antibody reactions is acquired and the biochemical reaction zone where information on a biochemical marker through an enzyme-substrate biochemical reaction is acquired are independently arranged on the same strip. With this arrangement, the hybrid biosensor of the present invention can simultaneously measure/analyze heterogeneous multiple biomarkers in a single sample in an independent manner, enabling accurate diagnosis and rapid analysis of a particular disease.

In addition, the sensor system of the present invention is a measurement and analysis system based on a smart device and can be operated for the on-site diagnosis and quantitative analysis of a particular disease in a convenient and economical manner.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Figure 1:
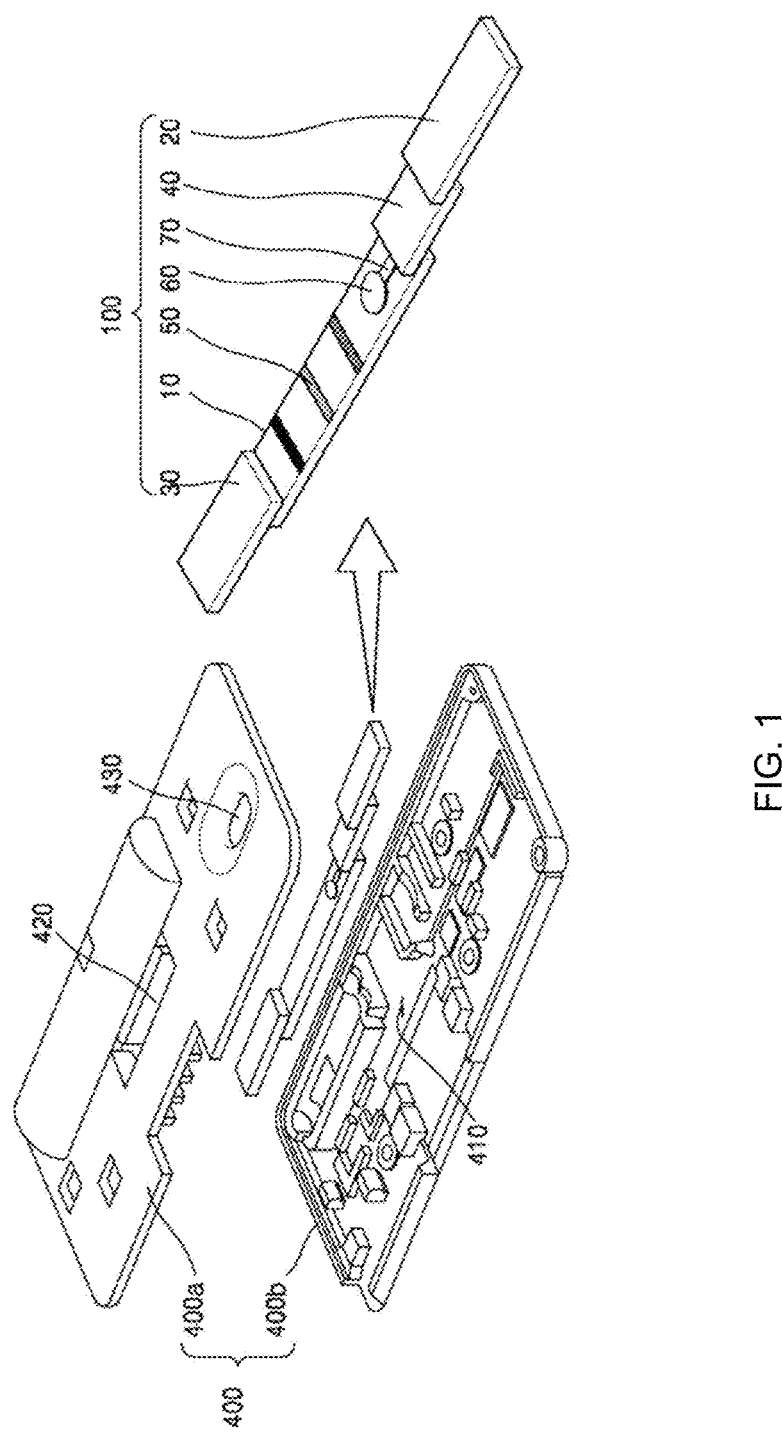
FIG. 1 is an exploded perspective view illustrating a biochemical-immunological hybrid biosensor according to an embodiment of the present invention.

Other objects, advantages, and novel features of the invention will become more apparent from the following detailed description and preferred embodiments with reference to the appended drawings. In the drawings, the same elements are denoted by the same reference numerals even though they are depicted in different drawings. Although such terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

Figure 2:
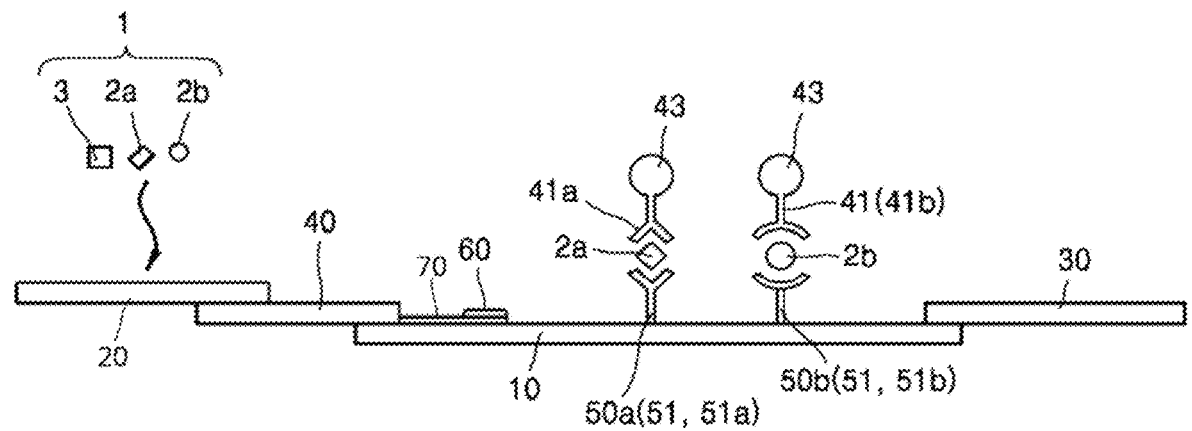
FIG. 2 is a cross-sectional view illustrating the principle of operation of a biochemical-immunological hybrid biosensor according to an embodiment of the present invention.
Figure 3:
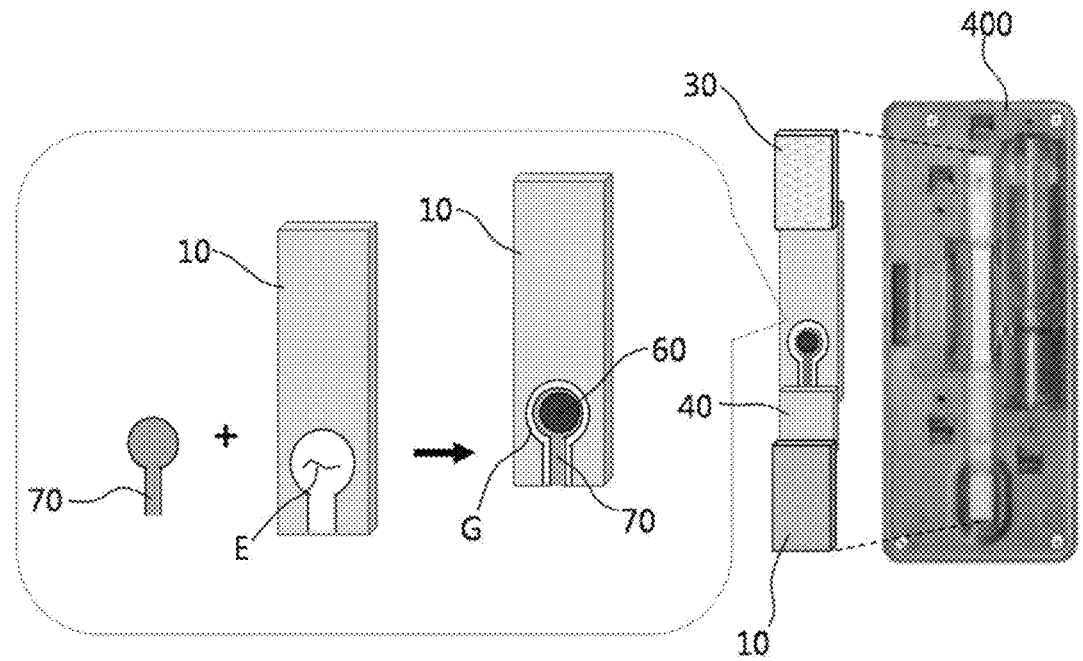
FIG. 3 is a detailed perspective view illustrating a reaction strip of the hybrid biosensor of FIG. 1.

FIG. 1 is an exploded perspective view illustrating a biochemical-immunological hybrid biosensor according to an embodiment of the present invention, FIG. 2 is a cross-sectional view illustrating the principle of operation of the biochemical-immunological hybrid biosensor, and FIG. 3 is a detailed perspective view illustrating a reaction strip of the hybrid biosensor.

As illustrated in FIGS. 1 and 2, the biochemical-immunological hybrid biosensor includes a reaction strip 100 in the form of a porous membrane through which a sample 1 moves by capillary action wherein the reaction strip 100 includes: a sample transfer pad 10 having a predetermined length and along which the sample 1 is transferred from one end to the other in the lengthwise direction; a sample addition pad 20 absorbing the sample 1 loaded from the outside; a conjugate pad 40 including detection antibodies 41 specifically binding to protein markers 2 in the sample 1 and a tracer 43 generating color signals for immunoreactions with the protein markers 2 and connecting one end of the sample transfer pad 10 to the sample addition pad 20; one or more immunoreaction zones 50 including capture antibodies 41 specifically binding to the protein markers 2 and formed on the sample transfer pad 10; at least one biochemical reaction zone 60, spatially separated from the sample transfer pad 10, including a chromogenic substrate generating a color signal for a biochemical reaction and at least one enzyme producing a product reacting with the chromogenic substrate from a biochemical marker 3 in the sample 1, receiving the sample 1 from at least one of the sample transfer pad 10, the sample addition pad 20, and the polymer pad 40, and where a biochemical reaction occurs independently from the reactions in the immunoreaction zones 50; and a sample absorption pad 30 arranged at the other end of the sample transfer pad 50 to absorb the sample 1 transferred along the sample transfer pad 10.

A lateral flow immuno-chromatographic assay (LF-ICA) for which a membrane strip is used is an immunoassay-based medical point-of-care-testing (POCT) technique. Herein, immuno-chromatography refers to a testing method based on a sandwich immunoassay that utilizes specific immunoreactivity of an antibody against an antigen, color developing properties and flow ability of colloidal gold, and migration of molecules by capillary action in a membrane. LF-ICA has the ability to detect the presence and concentration of an analyte in a sample within a short time even without using expensive equipment. Due to these advantages, LF-ICA is considered the most practical and is widely used in the POCT field. An immunosensor based on an immuno-chromatographic assay produces a color, which can be recognized by the naked eye, and requires only a very short time for analysis. Furthermore, an immunosensor based on an immuno-chromatographic assay can be used for the measurement of multiple protein biomarkers as well as single protein biomarkers. However, conventional immuno-biosensors for point-of-care-testing cannot acquire information on biochemical markers necessary to make a clinical decision regarding particular diseases simultaneously with information on protein markers. Thus, the use of separate assay systems is inevitable for the measurement of heterogeneous biomarkers. The biochemical-immunological hybrid biosensor of the present invention has been devised in an effort to solve the problems of conventional immunosensors.

The reaction strip 100 of the biochemical-immunological hybrid biosensor according to the present invention is in the form of a porous membrane through which the sample 1 moves by capillary action. Heterogeneous biomarkers in the sample 1 are independently detected by biochemical and immunological analysis techniques on the reaction strip 100.

Heterogeneous biomarkers are indicators of a disease incidence in the body. The protein markers 2 as heterogeneous biomarkers can be measured through antigen-antibody reactions and the biochemical marker 3 as another heterogeneous biomarker can be measured through an enzyme-substrate reaction. The number of the protein markers 2 is equal to or greater than 2 and therefore the reaction strip 100 can detect multiple biomarkers of the same type.

The heterogeneous multiple biomarkers detected in the reaction strip 100 are utilized as data for clinical decision-making for the diagnosis of a particular disease. For example, sepsis is diagnosed by measuring the concentrations of C-reactive protein (CRP) and procalcitonin (PCT) as the protein markers 2 and lactate as the biochemical marker 3. For another example, a cardiovascular disease is diagnosed by measuring myoglobin and cardiac troponin I as the protein markers 2 and cholesterol as the biochemical marker 3. For another example, urine albumin as the protein marker 2 and glucose as the biochemical marker 3 are measured for the diagnosis of diabetes complications.

Simultaneous analyses of the protein markers 2 and the biochemical marker 3 are required for the diagnosis of various diseases, as described above. The biochemical-immunological hybrid biosensor of the present invention is used mainly for the diagnosis of sepsis as a target disease. However, sepsis is illustrative only and is not intended to limit the effects, applications, and scope of the invention.

Specifically, the reaction strip 100 is constructed to include the sample transfer pad 10, the sample addition pad 20, the conjugate pad 40, the immunoreaction zone 50, the biochemical reaction zone 60, and the sample absorption pad 30. Due to this construction, the heterogeneous multiple biomarkers in the sample 1 can be detected by biochemical and immunological analysis techniques.

The sample transfer pad 10 has a predetermined length and the sample is transferred from one end to the other end of the sample transfer pad 10 in the lengthwise direction by capillary action. The flow of the sample 1 along the lengthwise direction is defined as a vertical or lengthwise flow. The sample 1 is blood or urine containing the protein markers 2 and the biochemical marker 3 and is loaded from the outside.

The sample addition pad 20 absorbs the loaded sample 1 and is connected to one end of the sample transfer pad 10 through the conjugate pad 40. The conjugate pad 40 is disposed on one end of the sample transfer pad 10 and the sample addition pad 20 is disposed on the other end of conjugate pad 40. However, this structure does not necessarily limit the scope of the invention. The connection structure may be modified such that the sample 1 can move sequentially through the sample addition pad 20, the conjugate pad 40, and the sample transfer pad 10. Due to this structure, the sample 1 absorbed into the sample addition pad 20 moves to the sample transfer pad 10 through the conjugate pad 40 by capillary action.

The detection antibodies 41 and the tracer 43 are present in the conjugate pad 40. Specifically, tracer-detection antibody conjugates are accumulated in a dry state in the conjugate pad 40. The detection antibodies 41 specifically bind to the protein markers 2 in the sample 1 and the tracer 43 conjugated to the detection antibodies 41 generates color signals in response to the concentrations of the protein markers 2. The tracer 43 may be colloidal gold that can be produced at low cost. The tracer 43 is not necessarily limited to colloidal gold. Any known tracer that can generate color signals in response to the concentrations of the protein markers 2 may be used.

The conjugates in a dry state are dissolved by the moving sample 1 and the detection antibodies 41 specifically bind to predetermined sites (first sites) of the protein markers 2 in the sample 1. After the primary reactions, the protein markers 2 bound to the conjugates move along the sample transfer pad 10 and generate color signals from the immunoreaction zones 50.

The immunoreaction zones 50 are formed in the sample transfer pad 10. The capture antibodies 51 specifically bind to other sites (second sites) of the conjugate-bound protein markers 2 in the immunoreaction zones 50. The tracer 43 generates specific color signals in response to the concentrations of the protein markers 2, enabling the analysis of the kinds and concentrations of the protein markers 2. Colloidal gold as the tracer 43 produces a red signal.

The number of the immunoreaction zones 50 is equal to or greater than 2 because the plurality of protein markers 2 need to be analyzed for the diagnosis of a particular disease. For example, when it is desired to analyze PCT 2a and CRP 2b as the protein markers 2 for the diagnosis of sepsis, two immunoreaction zones are formed. In this case, an anti-PCT capture antibody 51a is present in one of the immunoreaction zones 50 and an anti-CRP capture antibody 51b is present in the other immunoreaction zone 50 such that the capture antibodies bind to the different protein markers 2a and 2b in a one-to-one relationship in the immunoreaction zones.

The conjugate-bound PCT 2a and CRP 2b bind to the different capture antibodies 51a and 51b to generate different color signals from the different immunoreaction zones 50a and 50b, respectively. Since the first immunoreaction zone 50a including the anti-PCT capture antibody 51a and the second immunoreaction zone 50b including the anti-CRP capture antibody 51b are arranged at different positions, the presence or absence of PCT 2a and the CRP 2b can be determined depending on whether the corresponding color signals are generated at the positions.

On the other hand, the biochemical marker 3 is analyzed through an enzyme-substrate biochemical reaction in the spatially separated biochemical reaction zone 60 including a chromogenic substrate and an enzyme. The enzyme-substrate biochemical reaction occurs independently from the antigen-antibody reactions in the immunoreaction zones. In the presence of the biochemical marker 3 in sample 1, the enzyme produces a product reacting with the chromogenic substrate, and the chromogenic substrate generates a color signal in response to the biochemical reaction. The enzyme may be provided in plurality. In this case, the plurality of enzymes may also constitute an enzyme complex. The enzyme and the chromogenic substrate, accumulated in a dry state, are dissolved by the sample 1, and react with the biochemical marker 3.

Specifically, when lactate necessary for the diagnosis of sepsis is analyzed, the enzyme complex includes lactate oxidase (LOX) and horseradish peroxidase (HRP) and the chromogenic substrate may be potassium iodide. When the sample 1 reaches the biochemical reaction zone 60, hydrogen peroxide (first product) is produced in proportion to the concentration of lactate via a catalytic reaction of LOX and is converted into reactive oxygen (second product as reactant for the next reaction) via a catalytic reaction of HRP. The reactive oxygen reacts with colorless potassium iodide and the potassium iodide is oxidized to iodine to generate a brown signal. The color signal is generated in proportion to the concentration of lactate, which enables the determination of the presence and concentration of lactate.

The sample 1 used for the reactions in the biochemical reaction zone 60 is received from at least one of the sample transfer pad 10, the sample addition pad 20, and the conjugate pad 40. The reactions in the biochemical reaction zone 60 proceed independently from the reactions in the immunoreaction zones 50. The independent reactions are induced by spatially separating the biochemical reaction zone 60 from the sample transfer pad 10 in which the immunoreaction zones 50 are formed.

A biochemical reaction pad 70 may be used to connect the biochemical reaction zone 60 to at least one of the sample transfer pad 10, the sample addition pad 20, and the conjugate pad 40, and to support the biochemical reaction zone 60. The biochemical reaction pad 70 is in the form of a porous membrane. Here, the biochemical reaction pad 70 extends outward from the conjugate pad 40 toward the other end of the sample transfer pad 10. The biochemical reaction pad 70 is not necessarily connected to the conjugate pad 40 and may be connected to the sample transfer pad 10 and/or the sample addition pad 20. The biochemical reaction zone 60 is arranged on one side of the biochemical reaction pad 70. The biochemical reaction pad 70 may be disposed inside or outside the sample transfer pad 10, i.e., the biochemical reaction pad 70 may be provided in plurality.

The biochemical reaction zone 60 arranged on the biochemical reaction pad 70 is spaced apart from the outer surface of the sample transfer pad 10. That is, the biochemical reaction zone 60 is spatially separated from the sample transfer pad 10 except one end of the biochemical reaction pad 70 through which the sample 1 enters. As an example, the sample transfer pad 10 may be perforated along the thickness direction to form an accommodation portion E in which the biochemical reaction pad 70 is arranged, as illustrated in FIG. 3. A gap G is formed between the inner surface of the accommodation portion E and the edge of the biochemical reaction pad 70 to prevent contact therebetween such that the sample transfer pad 10 is spatially separated from the biochemical reaction zone 60. The biochemical reaction pad 70 may be arranged in the middle of the sample transfer pad 10 (not illustrated). Also in this case, a gap is formed between the two pads 10 and 70 except one end of the biochemical reaction pad 70 through which the sample 1 enters such that the sample transfer pad 10 is spatially separated from the biochemical reaction zone 60 after loading of the sample 1. As a result, the reactions in the biochemical reaction zone 60 are allowed to proceed independently without being influenced from vertical and horizontal flows caused by capillary action during analysis of the sample 1.

The accommodation portion E may be formed by etching the sample transfer pad 10 such that it has a shape corresponding to that of the biochemical reaction pad 70 and the biochemical reaction pad 70 is placed on the accommodation portion E leaving the gap G except the sample entrance. However, there is no particular restriction on the formation method and shape of the accommodation portion E. The sample transfer pad 10 is not necessarily perforated to form the accommodation portion E so long as the inner surface of the accommodation portion E is spaced apart from the outer surface of the biochemical reaction pad 70 over a predetermined area. The accommodation portion E may be concavely depressed from the outer surface of the sample transfer pad 10. The accommodation portion E is not necessarily provided for spatial separation and the biochemical reaction pad 70 may be spaced a distance from the outer surface of the sample transfer pad 10.

As described previously, the biochemical reaction pad 70 extends outward from at least one of the sample transfer pad 10, the sample addition pad 20, and the conjugate pad 40, and the sample transfer pad 10 formed with the immunoreaction zones 50 is connected to the conjugate pad 40 but is spatially separated from the biochemical reaction zone 60 over a predetermined area. Due to this structure, the sample 1 moving by capillary action is independently subjected to the biochemical reaction and immunoreactions along a single flow to generate respective color signals. The reaction strip 100 is defined as a "single fluidic strip" by its structure. The sample 1 having undergone the biochemical reaction and immunoreactions is absorbed into the sample absorption pad 30.

The sample 1 having undergone the biochemical reaction and immunoreactions is finally absorbed into the sample absorption pad 30 arranged on the other end of the sample transfer pad 10. The sample absorption pad 30 may be disposed on the other end of the sample transfer pad 10 but is not necessarily limited to this arrangement.

Taken together, the biochemical-immunological hybrid biosensor of the present invention has a structure in which the immunoreaction zones 50 where information on the protein markers 2 is acquired through the antigen-antibody reactions and the biochemical reaction zone 60 where information on the biochemical marker 3 is acquired through the enzyme-substrate biochemical reaction are arranged on the same strip. This structure enables the diagnosis of a disease from a single sample (e.g. blood) so that patient's pain, which is likely to be stressful, can be alleviated and allows for efficient use of the limited sample. In addition, the biochemical-immunological hybrid biosensor of the present invention can simultaneously measure heterogeneous multiple biomarkers in a single sample in an independent manner, enabling accurate diagnosis and rapid analysis of a disease. Furthermore, the biochemical-immunological hybrid biosensor of the present invention does not require time to render separate analyzers ready for operation so that the sample (e.g., blood) can be prevented from being contaminated. Moreover, the biochemical-immunological hybrid biosensor of the present invention can simultaneously measure disease-related biomarkers in several patients under urgent situations, for example, in emergency rooms of hospitals, and can analyze without imposing an economic burden on people from developing countries and ordinary people with low levels of income.

The biochemical-immunological hybrid biosensor of the present invention may further include a cartridge 400 accommodating the reaction strip 100. The cartridge 400 has an internal accommodation space 410 in which the reaction strip 100 is accommodated. The cartridge 400 is perforated to form a sample injection port 430 through which the accommodation space 410 is in communication with the outside and the sample 1 is introduced into the reaction strip 100 and a detection window 420 through which the immunoreaction zones 50 and the biochemical reaction zone 60 are exposed. Color signals from the reaction zones 50 and 60 can be observed from the outside through the detection window.

The cartridge 400 consists of a top plate 400a and a bottom plate 400b between which the reaction strip 100 is arranged. The top plate 400a can be coupled to the bottom plate 400b to fix the reaction strip 100 in the cartridge 400. However, the cartridge 400 may not necessarily consist of the top plate 400a and the bottom plate 400b. For example, the cartridge 400 may be produced in one piece in which the reaction strip 100 is inserted.

Hereinafter, a "branched fluidic strip" will be explained.

Figure 4:
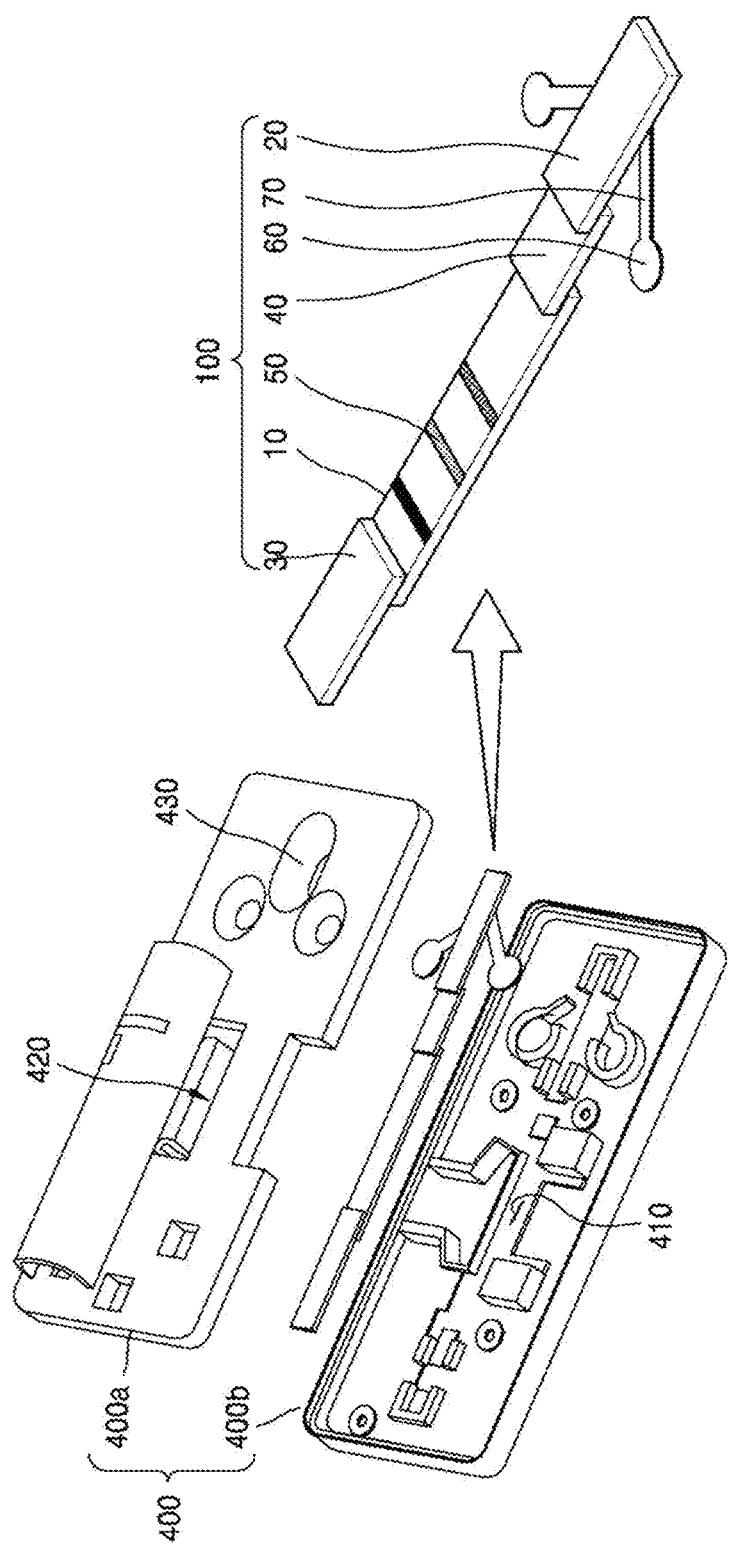
FIG. 4 is an exploded perspective view illustrating a biochemical-immunological hybrid biosensor according to a further embodiment of the present invention.

FIG. 4 is an exploded perspective view illustrating a biochemical-immunological hybrid biosensor according to a further embodiment of the present invention.

As illustrated in FIG. 4, a reaction strip 100 may include biochemical reaction pads 70 extending outward from a sample addition pad 20. The biochemical reaction pad 70 may be branched from the sample addition pad 20. A biochemical reaction zone 60 is arranged on one side of each of the biochemical reaction pads 70. This arrangement prevents the biochemical reaction zones 60 for the analysis of biochemical markers from being spatially restricted, facilitating the analysis of multiple biochemical markers.

On the other hand, the biochemical-immunological hybrid biosensor of the present invention needs to be washed after the antigen-antibody reactions. The washing is performed in a simple manner by a two-dimensional immunological immuno-chromatographic assay, which will be explained in detail below.

Figure 5:
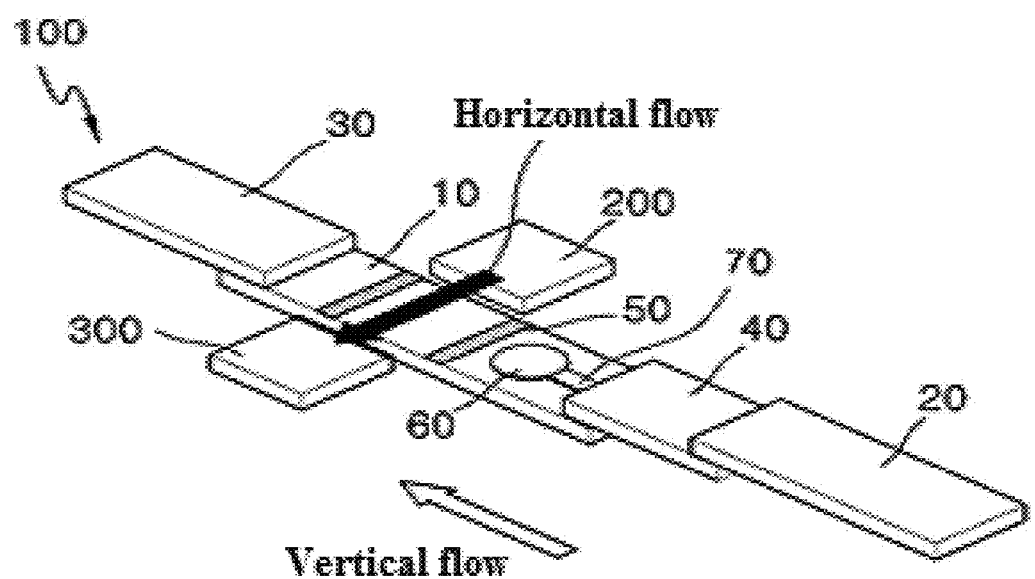
FIG. 5 is a perspective view illustrating a reaction strip of a biochemical-immunological hybrid biosensor according to another embodiment of the present invention.

FIG. 5 is a perspective view illustrating a reaction strip of a biochemical-immunological hybrid biosensor according to another embodiment of the present invention.

As illustrated in FIG. 5, the biochemical-immunological hybrid biosensor may further include a substrate addition pad 200 and a substrate absorption pad 300. The substrate addition pad 200 is in the form of a porous membrane that absorbs a substrate loaded from the outside. The substrate addition pad 200 is arranged adjacent to one lateral side of the sample transfer pad 10. The substrate absorption pad 300 is arranged at the other lateral side of the sample transfer pad 10. With this arrangement, the substrate moves across the sample transfer pad 10 from the substrate addition pad 200, that is, in the widthwise direction of the sample transfer pad 10, and is absorbed into the substrate absorption pad 300. The movement of the substrate is defined as a "horizontal or widthwise flow"). Since the substrate absorption pad 300 is exchanged during 2-dimensional immuno-chromatographic assay, the cartridge 400 is designed such that the substrate absorption pad 300 is easily detachable from the place where it is located.

Hereinafter, an explanation will be given of the 2-dimensional immuno-chromatographic assay. Particularly, the concentration of PCT as a marker for sepsis diagnosis in blood is 100 times lower than that of CRP. Thus, an enzyme tracer in which multiple molecules are prepared in the form of polymers can be used for highly sensitive diagnosis. The enzyme tracer may be horseradish peroxidase (HRP). To this end, the sample is first mixed with a biotinylated anti-PCT antibody. Thereafter, the sample is loaded through the sample injection port 430. The sample moves along the sample transfer pad 10 and reacts with the capture antibodies 51 in the immunoreaction zones 50 to form binding complexes. Then, a streptavidin-coupled polymerized enzyme tracer and a HRP-labeled anti-CRP antibody are sequentially loaded through a substrate injection port, which is formed by perforating the cartridge 400, to induce a primary cross-flow. The resulting mixture reacts with the binding complexes to form sandwich complexes including the enzyme tracer. Thereafter, the substrate absorption pad 300 is replaced with a new one and an HRP chromogenic substrate is supplied through the substrate injection port to create a secondary cross-flow. As a result, color signals are generated through the enzyme reactions from the immunoreaction zones 50 where PCT and CRP are measured.

As described above, the gap G in the form of an empty space is formed between the biochemical reaction pad 70 and the sample transfer pad 10 of the single fluidic strip (see FIG. 3). With this arrangement, the biochemical reaction is not affected by the horizontal flow. The empty space formed along the edge of the biochemical reaction pad 70 acts as a barrier to capillary action to prevent the horizontal flow of the substrate fluid from entering the biochemical reaction zone 60.

The biomarkers detected by the biochemical-immunological hybrid biosensor of the present invention can be analyzed simultaneously with on-site detection by using a signal detection system based on a smart device, which will be explained below.

Figure 6:
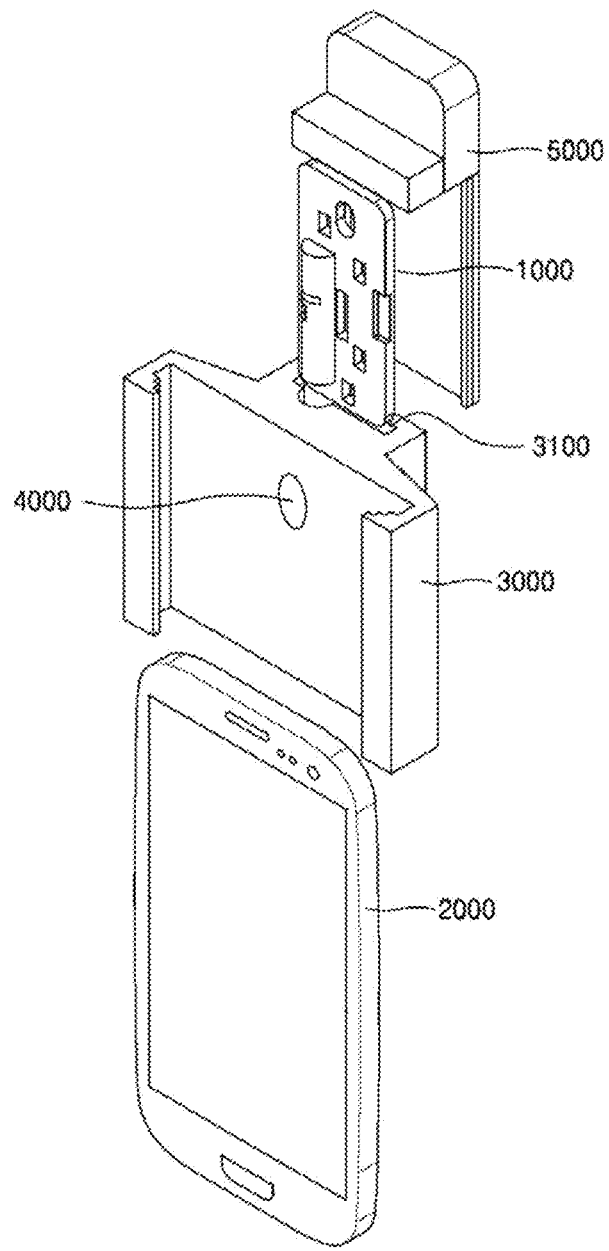
FIG. 6 is a perspective view illustrating a sensor system including a biochemical-immunological hybrid biosensor according to an embodiment of the present invention.

FIG. 6 is a perspective view illustrating a sensor system including a biochemical-immunological hybrid biosensor according to an embodiment of the present invention.

As illustrated in FIG. 6, the sensor system includes a biochemical-immunological hybrid biosensor 1000; a smart device 2000 in which a camera capable of capturing color signals from the immunoreaction zones 50 (see FIGS. 1 to 5) or a color signal from the biochemical reaction zone 60 (see FIGS. 1 to 5) as an image is accommodated; and a smart device holder 3000 having a slot 3100 into which the biochemical-immunological hybrid biosensor 1000 is inserted and adapted to hold the smart device 2000.

The biochemical-immunological hybrid biosensor 1000 is the same as that described above and a detailed description thereof is thus omitted. The smart device 2000 refers to a device, such as a smartphone, a tablet computer or a notebook computer, whose function is not limited and can be altered or extended to a considerable extent through an application program, such as a mobile application. The lens of the camera accommodated in the smart device 2000 is arranged to face the immunoreaction zones 50 and/or the biochemical reaction zone 60. With this arrangement, the camera can capture the color signals as an image. The smart device 2000 and the biochemical-immunological hybrid biosensor 1000 are held by the smart device holder 3000. The smart device holder 3000 has a stand holding the smart device 2000 and a slot 3100 into which the biochemical-immunological hybrid biosensor 1000 is inserted. The biochemical-immunological hybrid biosensor 1000 inserted into the slot 310 may be fixed by a cover 5000.

The sensor system of the present invention may further include a focusing lens 4000. The focusing lens 4000 is adapted to control the focal distance of the camera. The focusing lens 4000 can be arranged between the camera and the immunoreaction zone 50 and/or the biochemical reaction zone 60 to improve the resolution of the color signal image.

The sensor system of the present invention further includes a light source arranged in the smart device holder 3000. The light source may be, for example, an LED lamp. The light source can be automatically turned on when the smart device 2000 is held by the stand. The biochemical-immunological hybrid biosensor 1000 generates color signals by a biochemical reaction and immunoreactions is inserted into the slot 3100 and the camera can capture the color signals generated from the biochemical-immunological hybrid biosensor 1000 as an image.

The captured image is converted into digital data, which can be utilized as information for quantitative analysis. The conversion into digital data can be accomplished by a suitable application on the smart device 2000.

Overall, the sensor system of the present invention is an analytical system based on a smart device and can be operated for the on-site diagnosis and quantitative analysis of a particular disease in a convenient and economical manner.

The present invention will be explained in more detail with reference to the following examples. These examples are merely illustrative and the scope of the present invention is not limited thereto.

Figure 7:
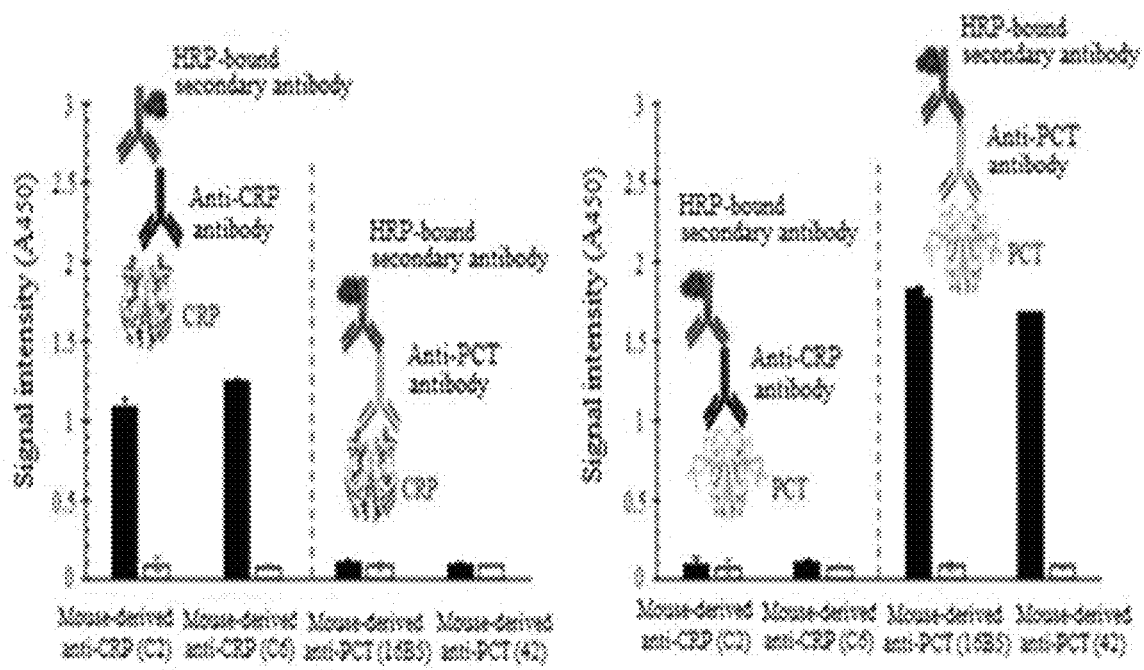
FIG. 7 shows reaction specificities of different types of capture antibodies.
Figure 8:
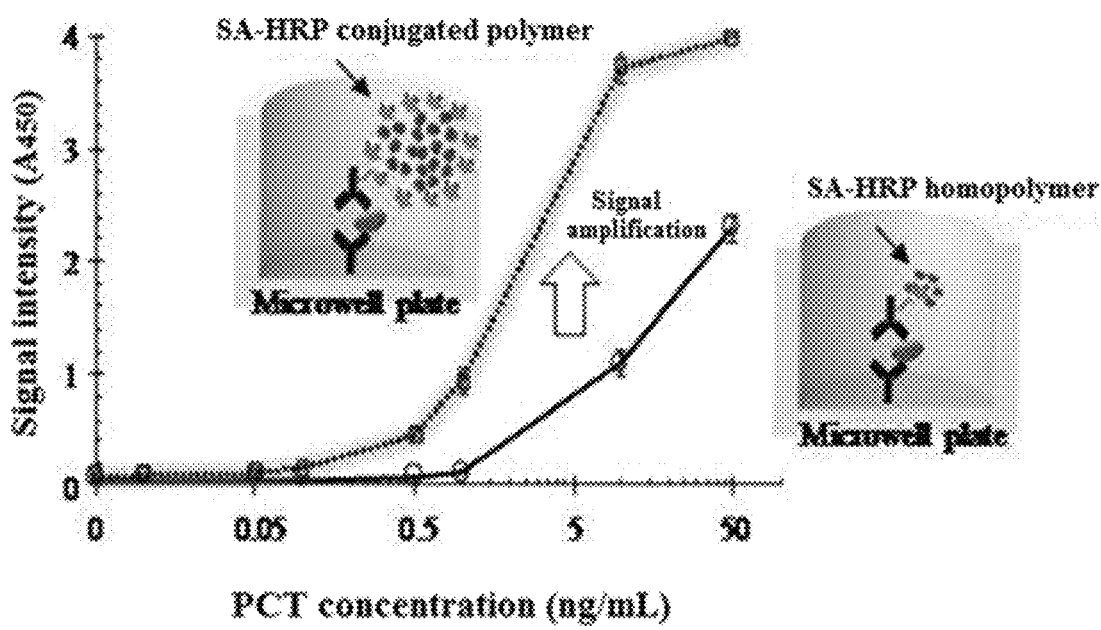
FIG. 8 shows signal intensities as a function of PCT concentration when a SA-HRP conjugated polymer and a SA-HRP homopolymer were used as sandwich ELISA signal sources.
Figure 9:
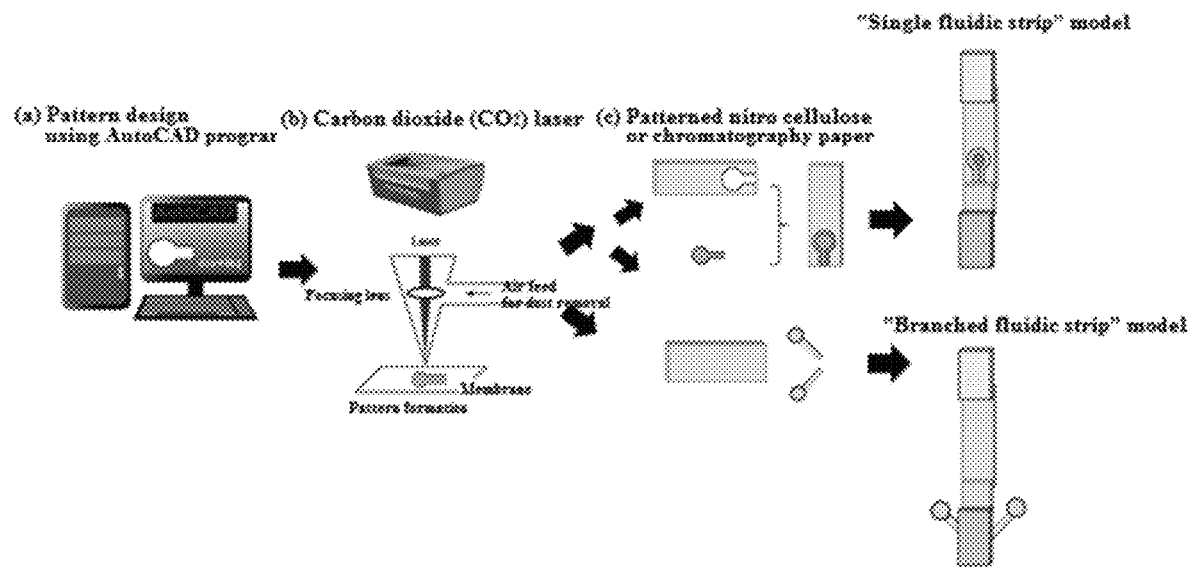
FIG. 9 is a process diagram showing a procedure for constructing a membrane reaction strip for biochemical-immunoassays according to the present invention.
Figure 10:
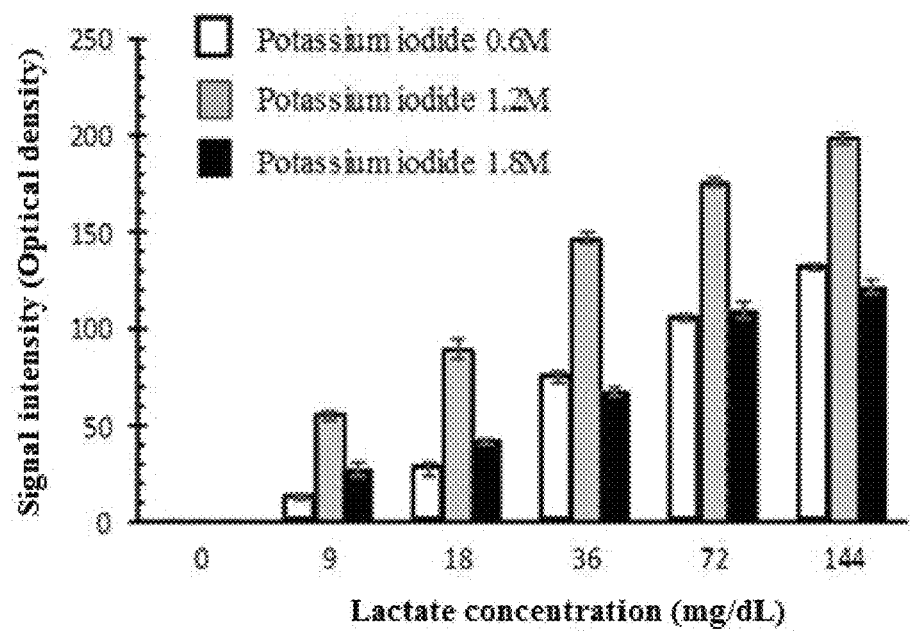
FIG. 10 shows lactate dose responses of a biochemical-immunological hybrid biosensor according to the present invention at different concentrations of a chromogenic substrate.
Figure 11:
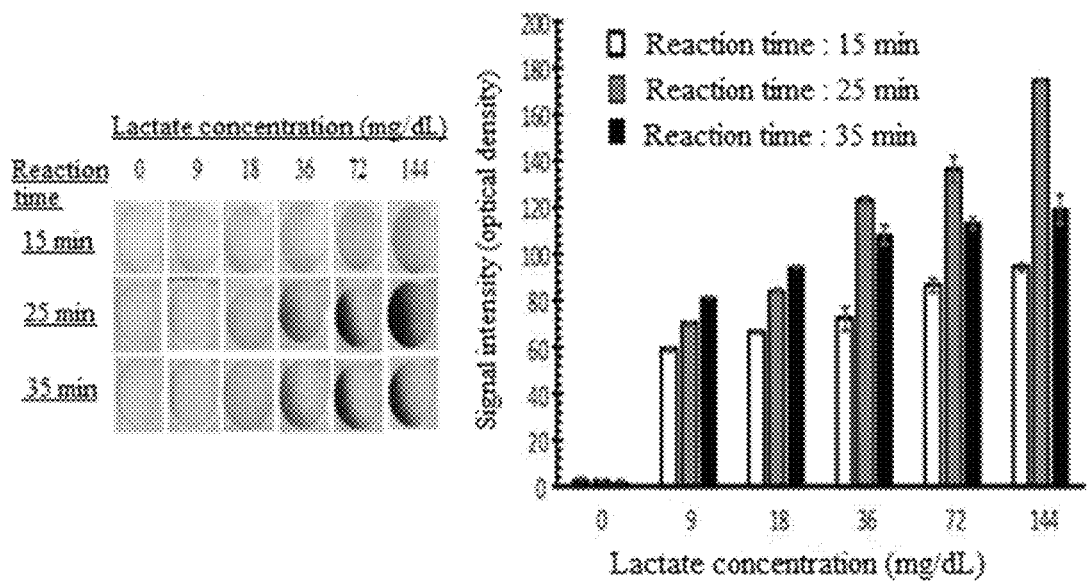
FIG. 11 shows lactate dose responses of a biochemical-immunological hybrid biosensor according to the present invention for different reaction times.
Figure 12:
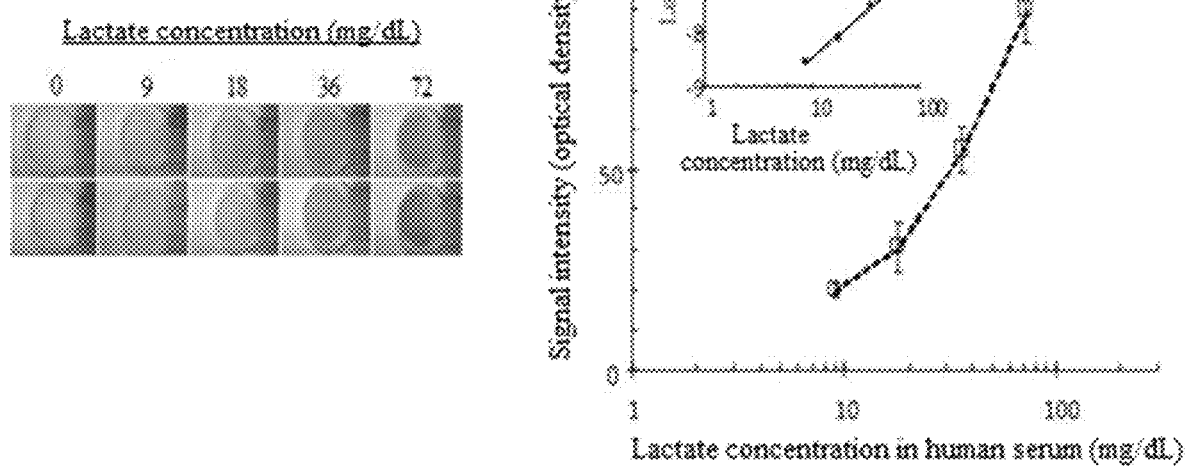
FIG. 12 shows a dose-response curve of a biochemical-immunological hybrid biosensor according to the present invention for lactate under optimal conditions.
Figure 13:
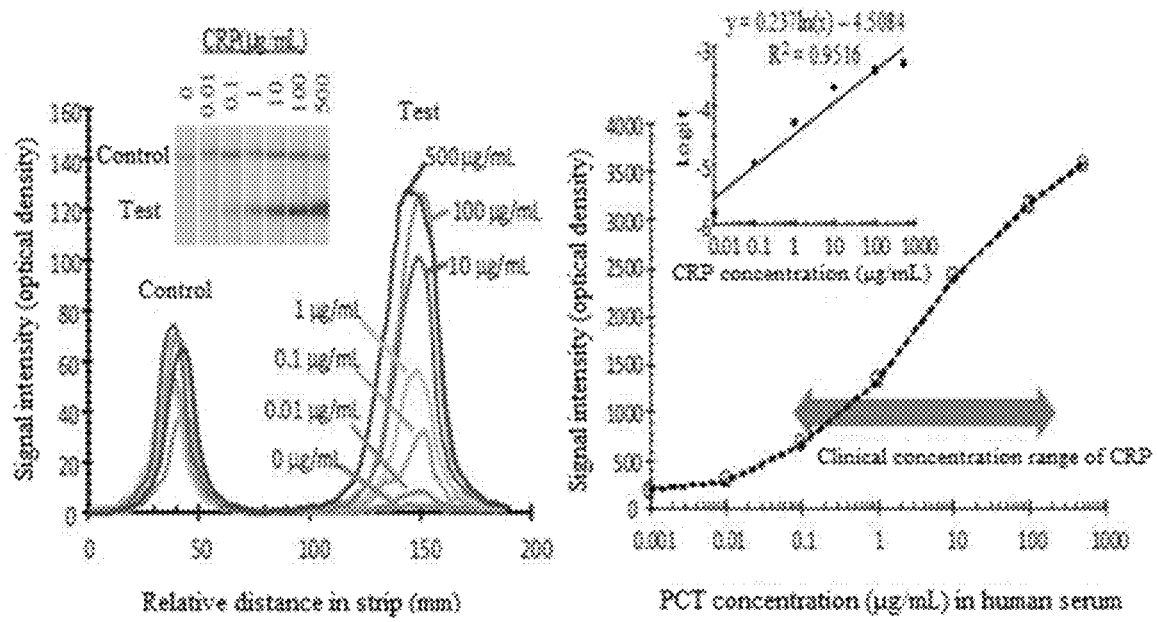
FIG. 13 shows a dose-response curve of a biochemical-immunological hybrid biosensor according to the present invention for CRP under optimal conditions.
Figure 14:
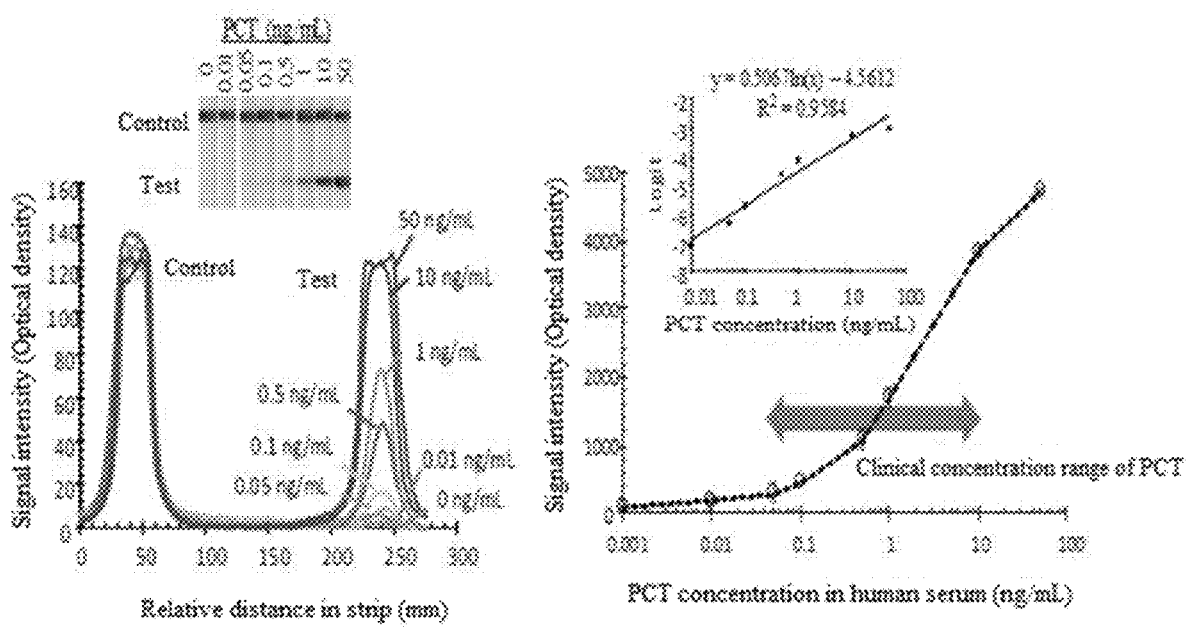
FIG. 14 shows a dose-response curve of a biochemical-immunological hybrid biosensor according to the present invention for PCT under optimal conditions.
Figure 15:
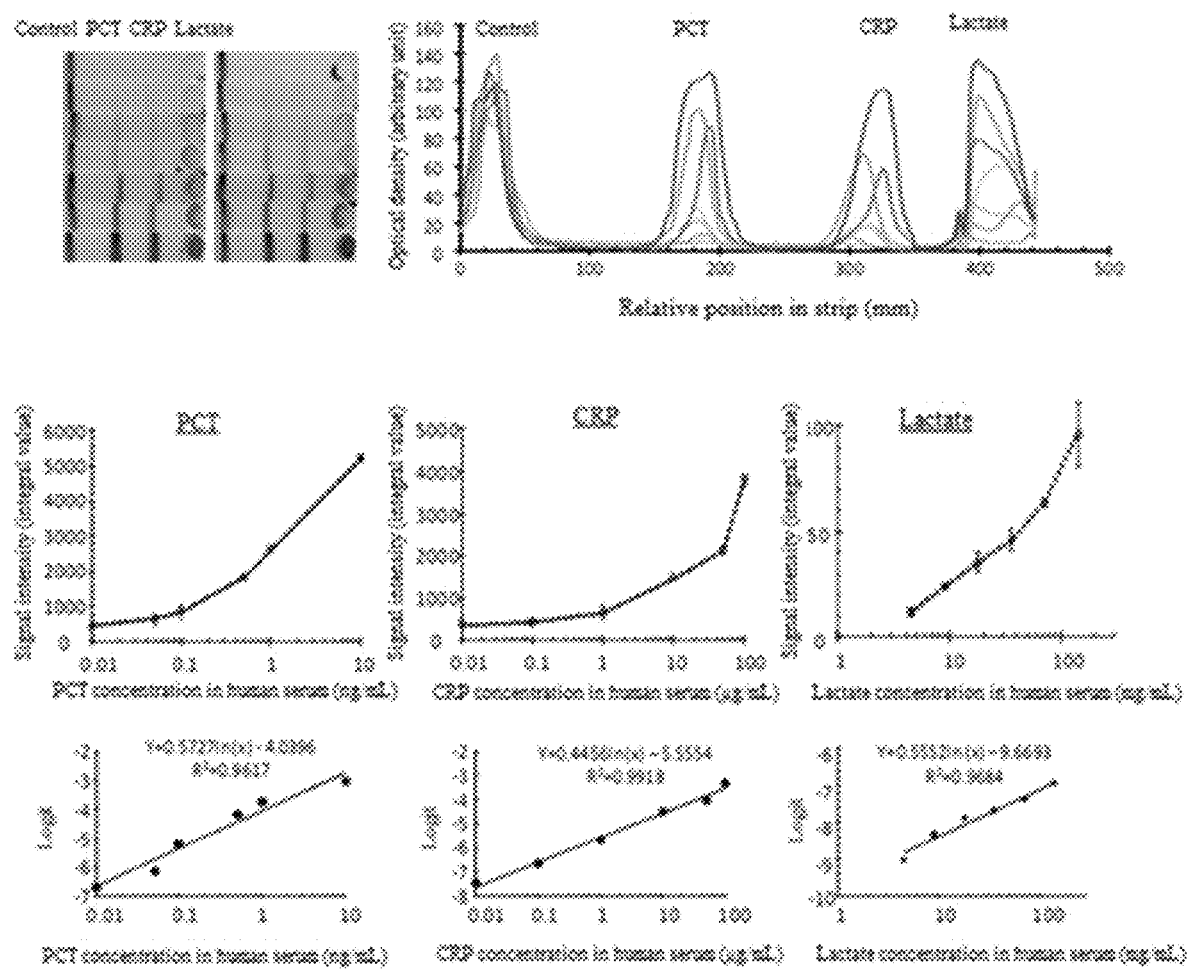
FIG. 15 shows the results obtained by simultaneous analyses of PCT, CRP, and lactate using a biochemical-immunological hybrid biosensor according to the present invention.

FIG. 7 shows reaction specificities of different types of capture antibodies, FIG. 8 shows signal intensities as a function of PCT concentration when a SA-polymeric HRP conjugate and a SA-single HRP conjugate were used as sandwich ELISA tracers, FIG. 9 is a process diagram showing a procedure for constructing a membrane reaction strip for biochemical-immunological assays according to the present invention, FIG. 10 shows lactate dose responses of a biochemical-immunological hybrid biosensor according to the present invention at different concentrations of a chromogenic substrate, FIG. 11 shows lactate dose responses of a biochemical-immunological hybrid biosensor according to the present invention for different reaction times, FIG. 12 shows a dose-response curve of a biochemical-immunological hybrid biosensor according to the present invention for lactate under optimal conditions, FIG. 13 shows a dose-response curve of a biochemical-immunological hybrid biosensor according to the present invention for CRP under optimal conditions, FIG. 14 shows a dose-response curve of a biochemical-immunological hybrid biosensor according to the present invention for PCT under optimal conditions, and FIG. 15 shows the results obtained by simultaneous analyses of PCT, CRP, and lactate using a biochemical-immunological hybrid biosensor according to the present invention.

EXAMPLE

Experimental Materials

Materials used in the following examples and their manufacturers are as follows. Human procalcitonin (PCT) standard samples, anti-human PCT monoclonal antibodies (Clones 1665 and 42), and anti-human CRP monoclonal antibodies (Clones C2 and C6) were purchased from Hytest Ltd. (Finland). Human CRP standard samples were purchased from Cliniqa Corp. (USA). Goat anti-mouse IgG antibodies, sulfosuccinimidyl-6-[biotinamido]-6-hexanamido hexanoate (NHS-LC-LC biotin), cyclohexane-1-carboxylate (SMCC), sulfosuccinimidyl 6-[3'-(2-pyridyldithio)propionamido]hexanoate (sulfo-LC-SPDP), and dithiothreitol (DTT) were purchased from ThermoFisher Scientific (USA). Sodium, L-lactate, lactate oxidase (LOX) from *pediococcus* sp., potassium iodide, casein, sodium phosphate monobasic, sodium phosphate, Tween20, sodium acetate, sodium chloride, hydrogen peroxide, and tetramethyl benzidine (TMB) were purchased from Sigma (USA). Cellulose membranes (17 CHR Chromatography grade) and cellulose chromatography papers (grade 1 Chr) were purchased from Whatman (UK). Glass membranes (PT-R5) and sample application pads (Grade 319) were purchased from MDI (Gurgaon, India). Horseradish peroxidase (HRP), TMB for membrane applications (TMBM), streptavidin-poly HRP20, and nitro cellulose membranes (HiFlowPlus HFB13504) were purchased from Calbiochem (USA), Moss (USA), Fitzgerald (USA), and Millipore (USA), respectively. All reagents were of analytical grade.

Example 1: Characterization of Specific Reactivities of Antibodies

For cross-reactivity testing, the CRP and PCT standard substances were diluted to 5 μg/mL with 10 mM phosphate buffered saline (10 mM PBS). Thereafter, 100 μL of each of the solutions of the CRP and PCT standard substances was plated in microwells and coated on the microwells at 37° C. for 2 h. The microwells were washed three times with deionized water (DIW) to remove unreacted standard substances. Thereafter, the surface of the microwells uncoated with the standard substances was coated by plating 20 µL of 0.5% casein solution diluted with 10 mM PBS in the microwells, followed by treatment at 37° C. for 2 h. The microwells were washed three times with DIW to remove remaining casein. The monoclonal antibodies for the CRP and PCT standard substances were diluted to 1 µg/mL with a buffer (casein PBS-TW), which has been previously prepared by adding 0.1% tween 20 to 0.5% casein PBS. The solutions (100 µL each) were plated in the microwells. Thereafter, the antigen-antibody reactions were allowed to proceed at 37° C. for 1 h. The microwells were washed three times with DIW to remove unreacted monoclonal antibodies for the CRP and PCT standard substances. Thereafter, a 0.5 µg/mL HRP-labeled goat anti-mouse antibody was diluted with casein PBS-TW solution and 10 µL of the solution was plated in the microwells. The reaction was allowed to proceed at 37° C. for 1 h. The microwells were washed three times with DIW to remove to remove unreacted HRP-labeled goat anti-mouse antibody. For signal generation, 20 µL of an enzyme substrate (50 mM sodium acetate: 1% (w/v) TMB: 3% (w/v) hydrogen peroxide=1000:10:1) was plated in the microwells and color production was induced for 15 min. Thereafter, 50 µL of 2 M sulfuric acid solution was added to the microwells and the optical densities were measured at a wavelength of 450 nm using a micro plate reader (Synergy™ H4, BioTek Inc; Winooski, Vt.).

In accordance with the above analytical procedure, the antibody specificity that is one of the most critical immunoassay factors was examined using an indirect ELISA. The antigens, CRP and PCT, were separately coated on the microwell surfaces and capture antibodies (anti-CRP and anti-PCT) and HRP-bound detection antibodies (anti-mouse) were sequentially allowed to react with the respective antigens. As a result, when the two antibodies (clone; C2, C6) for CRP analysis and the two antibodies (clone; 1665, 42) for PCT analysis were used, their specificities to the respective analytes, CRP and PCT, were very high and no background signals were observed from other antibodies against the antigens, indicating the absence of cross-reactions (see FIG. 7). Therefore, it was determined that when simultaneous immunoassays for the standard substances, CRP and PCT, are conducted, no cross-reactions are present.

Example 2: Biotinylation of Anti-PCT Antibody

Succinimidyl residue of the biotin linker (NHS-LC-LC biotin) can react with a primary amine present in the antibody to form a biotinylated antibody. Four hundreds µg of the anti-PCT monoclonal antibody diluted with 10 mM PBS was mixed with 20-fold molar excess of NHS-LC-LC biotin and the mixture was allowed to react at room temperature for 2 h. Unreacted NHS-LC-LC biotin was removed by size exclusion gel chromatography with a Sephadex G-15 column (volume 10 mL). Thereafter, the antibody-biotin conjugate was diluted twice with 10 mM PBS and concentrated by centrifugation using Vivaspin™. The resulting antibody-biotin conjugate (1.5 mg/mL) was stored at 4° C. before use.

Example 3: Conjugation of Streptavidin with HRP

Streptavidin was activated with SMCC dissolved in 30-fold molar excess of DMSO at room temperature for 2 h. The excess SMCC was removed by size exclusion gel chromatography (Sephadex G-15). HRP was reacted with 25-fold molar excess of sulfo-LC-SPDP and activated through DTT reduction (final volume 10 mM). The remaining linker and DTT were separated through a Sephadex G-15 column. Thereafter, the SMCC linker-coupled streptavidin was reacted with the activated HRP at room temperature for 4 h. The resulting conjugate was mixed with glycerol (final concentration 50%) and stored at −20° C.

Example 4: Conjugation of Anti-CRP Antibody with HRP

The mouse-derived anti-CRP monoclonal antibody (clone C2) was conjugated with HRP in the same manner as mentioned above. The anti-CRP antibody was activated with SMCC dissolved in 30-fold molar excess of DMSO at room temperature for 2 h. The excess SMCC was removed by size exclusion gel chromatography (Sephadex G-15). HRP was reacted with 25-fold molar excess of sulfo-LC-SPDP and activated through DTT reduction (final volume 10 mM). The remaining linker and DTT were separated through a Sephadex G-15 column. Thereafter, the SMCC-activated anti-CRP antibody was reacted with the activated HRP at room temperature for 4 h. The resulting polymer was mixed with glycerol (final concentration 50%) and stored at −20° C.

Example 5: Preparation of Membrane Reaction Strip for Biochemical-Immunoassays

A hybrid biosensor composed of five functional membranes capable of simultaneously performing an immunoassay based on antigen-antibody reactions and a biochemical assay based on an enzyme reaction (see FIGS. 1 and 4) was constructed. A glass fiber membrane (4×17 mm, grade 319), a polyester membrane (4 mm×10, PT-R5), a nitro cellulose membrane (4×25 mm; HF13504), and a cellulose membrane (4×15 mm, 17 CHR) were used as a sample addition pad, a conjugate pad, a sample transfer pad, and a sample absorption pad, respectively.

Referring to FIG. 9, a biochemical reaction pad was prepared by molding a cellulose chromatography paper (2×3 mm+R=1.5 mm, grade 1 Chr). Specifically, the cellulose chromatography membrane was patterned into a predetermined shape using an AutoCAD program. Then, the patterned cellulose chromatography membrane was cut using $CO_2$ laser (VLS 2.30 universal laser) to construct the biochemical reaction pad (pixel per inch: 500, laser power: 10% and head speed: 50%).

For a single fluidic strip, the biochemical reaction pad was arranged in an accommodation portion of the sample transfer pad. Specifically, one end area of the sample transfer pad in which the accommodation portion was formed was designed to have a predetermined pattern using the same program. The pattern of the accommodation portion was designed to be larger by ~0.25 mm than the biochemical reaction pad such that a gap was formed between the edge of the biochemical reaction pad and the inner surface of the accommodation portion. The nitro cellulose in the patterned portion was removed by etching with $CO_2$ laser along the designed pattern such that the plastic support plate protruded to form the accommodation portion. Then, the biochemical reaction pad was aligned with one end of the sample transfer pad such that it was located in the accommodation portion. The biochemical reaction pad was attached to the plastic support plate using a double-sided adhesive tape. The inner surface of the accommodation portion of the sample transfer pad was spaced a distance of ~0.25 mm from the biochemical reaction pad to form an empty space therebetween.

To immobilize the capture antibodies for CRP and PCT, the anti-PCT antibody (1 mg/mL) and the anti-CRP antibody (0.5 mg/mL) were diluted with a 100 mM PB buffer containing 3% trehalose and were independently applied to the nitro cellulose membrane (1.5 μL/cm) using a micro-dispenser (BioJet 3000, Biodot, Irvine, Calif.). As a control, the goat-derived anti-mouse antibody (0.2 mg/mL) was applied to the nitro cellulose membrane using a micro-dispenser. The applied capture antibodies were located from the bottom in the order of the anti-CRP antibody, the anti-PCT antibody, and the goat-derived anti-mouse antibody. Thereafter, the membrane was dried at 37° C. for 1 h and stored in a dryer before use. The biotinylated anti-PCT antibody (0.1 mg/mL) was diluted with a 100 mM PB buffer containing 3% trehalose, applied, and dried at 37° C. for 1 h to construct the conjugate pad. An enzyme-substrate mixture composed of lactate oxidase (LOX), horseradish peroxidase (HRP), and potassium iodide was applied to the cellulose chromatography paper as a reaction layer for biochemical assay where a biochemical reaction was performed. For assembly, the functional membranes thus prepared were arranged such that they partially overlapped.

Example 6: Construction of Hybrid Biosensor Cartridge

In this example, a plastic cartridge (WLH 76×32×8 mm) for a hybrid biosensor consisting of a top plate and a bottom plate was constructed (see FIGS. 1 and 4). The top plate and the bottom plate were made of transparent polycarbonate. Two channels were formed in the bottom plate. The first channel was formed in the vertical direction to fix the reaction strip such that fluid was allowed to flow in the lengthwise flow. The second channel was formed in the horizontal direction such that the HRP-bound anti-CRP antibody, the SA-HRP conjugate, and the chromogenic substrate were supplied through the sample transfer pad. A window and an injection port were formed in the top plate. Colors produced as a result of the biochemical assay and the immunoassay can be observed through the window and a sample and a substrate solution can be supplied through the injection port. The assembled hybrid membrane reaction strip for simultaneous biochemical-immunological assays was arranged in the lengthwise flow channel and the absorption pad (13×10.5 mm, 17 CHR) capable of inducing a cross-flow was arranged in the horizontal channel. Thereafter, the bottom plate and the top plate were firmly coupled to each other through a joint without using an adhesive and were stored in a dryer at room temperature before use.

Example 7: Construction of Smartphone Plastic Holder for the Hybrid EOC Sensor In this example, a plastic holder dedicated to a smartphone (WLH is 150.2×76.1×9.4 mm; G-pro, LG electronics) was constructed. First, a plastic holder into which a hybrid EOC cartridge (WLH is 170×40×43 mm) is insertable was designed using a drawing program (Solidworks™, version 2012). The plastic holder was constructed using a 3D-pinter (MakerBot Replicator 2). An ABS resin was used as a material for the plastic holder. A white LED lamp using an AA size battery was mounted in the plastic holder to provide a controlled amount of light to the hybrid EOC cartridge.

Example 8: Establishment of Conditions for Lactate Analysis

The amounts of LOX, HRP, and potassium iodide were adjusted depending on reaction time to establish optimal conditions for lactate analysis. An observation was made by varying the concentrations of the enzyme complex (LOX, HRP) and the chromogenic substrate (potassium iodide) in the ranges of 200-1500 units/mL and 0.6-1.8 M, respectively. The test time was adjusted to 35 min to determine an optimal reaction time. Such quantitative variables were measured by drying the enzyme complex (0.3 μL) diluted with 0.5% BSA and 1% trehalose and the chromogenic substrate (0.3 μL) on laser-patterned cellulose chromatography paper at 37° C. for 1 h. A signal produced by the enzyme-substrate biochemical reactions was quantitatively analyzed using an image analyzer installed in the smartphone.

The optimal concentration (600 unit/mL) of the enzyme complex could be determined using the "single fluidic strip" model of FIG. 1. When the concentration of the enzyme complex was lower or higher than the optimal concentration, the signal intensity was decreased or non-specific signals were generated. The optimal concentration of the chromogenic substrate potassium iodide as another factor controlling the color signal was determined to be 1.2 M at the optimal concentration of the enzyme complex (see FIG. 8). Under these optimal conditions, the optimal reaction time for lactate analysis was found to be 25 min after initiation of the reaction (see FIG. 11). Based on the optimal conditions, the dose responses of the hybrid biosensor for lactate at various concentrations were obtained. As a result, signals in proportion to the concentration variation were measured and plotted to obtain a dose response curve, which was linearized via a log-logit transformation (see FIG. 12).

Example 9: Establishment of Conditions for CRP and PCT Immunoassays

The performances of single immunoassays for two protein markers, CRP and PCT, for sepsis diagnosis were tested. The standard substances (30 mg/mL CRP and 10 μg/mL PCT) were serially diluted with human serum to prepare standard samples having a concentration of 0.01-500 μg/mL for CRP and 0.01-10 μg/mL for PCT. Each sample (100 μL) was added to the sample addition pad in the biosensor cartridge and its vertical flow was maintained for 15 min. Thereafter, the HRP-bound anti-CRP antibody (0.025 μg/mL) for CRP and the streptavidin-poly HRP20 (0.066 ng/mL) for PCT were dissolved in a PBS solution containing 0.5% casein and 0.1% tween (Casein-PBS-Tw; 200 μL). Immediately after the dissolution, the resulting solution was added to the cartridge through the substrate solution injection port. After its widthwise flow was maintained for 5 min, the HRP enzyme substrate solution (200 μL) was supplied and an additional reaction time of 5 min was maintained.

Dose responses of the hybrid biosensor were measured under the respective optimal conditions for CRP and PCT immunoassays. As a result, signals were generated in proportion to the clinical concentration range (0.1-100 μg/mL) for CRP (see FIG. 13). The dose response curve was linearized via a log-logit transformation. These results concluded that the developed hybrid biosensor can be used for clinical analysis of CRP. The dose response range of PCT was also found to cover the clinical concentration range of the PCT marker (0.1-10 ng/mL) in terms of sepsis, indicating that the developed hybrid biosensor can be used for clinical analysis of PCT (see FIG. 14).

Example 10: Simultaneous Analyses of CRP, PCT, and Lactate Concentrations in the Same Sample The three biomarkers, CRP, PCT, and lactate, were simultaneously analyzed using the sensor system including the hybrid biosensor. To this end, standard substances for the biomarkers were prepared in which they were present at concentrations of 0.01-10 ng/mL for PCT, 0.1-500 μg/mL for CRP, and 9-144 mg/dL for lactate in the same human serum sample. The sample solution (100 μL) including the three biomarkers was plated on the sample addition pad and its lengthwise (vertical) flow was maintained for 15 min. During the lengthwise flow, an enzyme-substrate reaction for lactate analysis occurred in the reaction layer for biochemical assay. A color was produced depending on the concentrations of lactate. Thereafter, the HRP-bound anti-CRP antibody and the streptavidin-poly HRP20 (0.066 ng/mL) diluted with the casein-PBS-Tw solution were plated in the substrate injection port and the reaction was allowed by proceeding the horizontal flow for 5 min. For color signal generation, the TMBM substrate (200 μL) was plated in the substrate injection port and chromogenic reactions were performed for 5 min.

The dose response curves for the three markers were analyzed. As a result, the signals were found to increase in proportion to the concentrations of the markers. The signal intensities for the respective concentrations were distinguished from each other (see FIG. 15). For quantitative analysis, the dose response curves were linearized via a log-logit transformation. The analytical results obtained using the hybrid biosensor system revealed that the hybrid biosensor enables simultaneous quantitative analyses for the concentrations of the three biomarkers present in an unknown sample.

Although the present invention has been described herein with reference to the specific embodiments, these embodiments do not serve to limit the invention and are set forth for illustrative purposes. It will be apparent to those skilled in the art that modifications and improvements can be made without departing from the spirit and scope of the invention.

Such simple modifications and improvements of the present invention belong to the scope of the present invention, and the specific scope of the present invention will be clearly defined by the appended claims.

What is claimed is:

1. A biochemical-immunological hybrid biosensor comprising a reaction strip in the form of a porous membrane through which a sample moves by capillary action wherein the reaction strip comprises: a sample transfer pad having a predetermined length and along which the sample is transferred from one end to the other in the lengthwise direction; a sample addition pad absorbing the sample loaded from the outside; a conjugate pad comprising detection antibodies specifically binding to protein markers in the sample and a tracer generating color signals for immunoreactions with the protein markers, and connecting one end of the sample transfer pad to the sample addition pad; one or more immunoreaction zones, formed on the sample transfer pad, comprising capture antibodies specifically binding to the protein markers; at least one biochemical reaction zone comprising a chromogenic substrate generating a color signal for a biochemical reaction and at least one enzyme producing a product reacting with the chromogenic substrate from a biochemical marker in the sample which is received from at least one of the sample transfer pad, the sample addition pad, and the conjugate pad, and where a biochemical reaction occurs independently from the reactions in the immunoreaction zones; a sample absorption pad arranged at the other end of the sample transfer pad to absorb the sample transferred along the sample transfer pad; and at least one biochemical reaction pad extending outward from at least one of the sample transfer pad, the sample addition pad, and the conjugate pad, and the biochemical reaction zone is arranged on one side of the biochemical reaction pad, wherein the detection antibodies are conjugated with the tracer, wherein some of the sample are transferred to the sample transfer pad through the conjugate pad, and some of the sample are transferred to the biochemical reaction pad, wherein the protein markers bound the detection antibodies conjugated with the tracer generating color signals are bound to the capture antibodies, so that the color signals for immunoreactions are generated in the immunoreaction zones, wherein the biochemical marker in the sample reacts with the enzyme and the chromogenic substrate, so that the color signal for the biochemical reaction is generated in the biochemical reaction zone.

2. The biochemical-immunological hybrid biosensor according to claim 1, wherein the biochemical reaction zone is provided in plurality.

3. The biochemical-immunological hybrid biosensor according to claim 1, wherein the conjugate pad is disposed on one end of the sample transfer pad, the sample addition pad is disposed on the conjugate pad, and the sample absorption pad is disposed on the other end of the sample transfer pad.

4. The biochemical-immunological hybrid biosensor according to claim 1, wherein the number of the immunoreaction zones is equal to or greater than 2, and the capture antibodies bind to the protein markers in a one-to-one relationship in the immunoreaction zones.

5. The biochemical-immunological hybrid biosensor according to claim 1, wherein the protein markers are C-reactive protein (CRP) and procalcitonin (PCT), the biochemical marker is lactate, the enzyme is an enzyme complex of lactate oxidase (LOX) and horseradish peroxidase (HRP), the chromogenic substrate is potassium iodide, and the hybrid biosensor diagnoses sepsis.

6. The biochemical-immunological hybrid biosensor according to claim 1, further comprising a substrate addition pad disposed adjacent to one lateral side of the sample transfer pad to supply a substrate loaded from the outside and a substrate absorption pad disposed adjacent to the other lateral side of the sample transfer pad to absorb the substrate transferred across the sample transfer pad.

7. The biochemical-immunological hybrid biosensor according to claim 1, further comprising a cartridge having an accommodation space in which the reaction strip is arranged, a detection window through which the immunoreaction zone and the biochemical reaction zone are exposed, and a sample injection port through which the sample is loaded into the sample addition pad.

8. A sensor system comprising: the biochemical-immunological hybrid biosensor according to claim 1; a smart device in which a camera capable of capturing color signals from the immunoreaction zones or a color signal from the biochemical reaction zone as an image is accommodated; and a smart device holder having a slot into which the biochemical-immunological hybrid biosensor is inserted and adapted to hold the smart device.

9. The sensor system according to claim 8, further comprising a light source arranged in the smart device holder to emit light.

10. The sensor system according to claim 8, wherein the captured image of the color signals is converted into digital data by an application on the smart device.

11. The sensor system according to claim 8, further comprising a focusing lens arranged between the camera and the immunoreaction zone or the biochemical reaction zone to control the focal distance of the camera.

* * * * *